United States Patent
Chandross et al.

(10) Patent No.: US 7,332,627 B2
(45) Date of Patent: Feb. 19, 2008

(54) COMPOSITIONS COMPRISING A SOLVATED METAL

(75) Inventors: Edwin Arthur Chandross, Murray Hill, NJ (US); Ramaswamy Srinivasa Raghavan, Berkeley Heights, NJ (US)

(73) Assignee: Lucent Technologies Inc., Murray Hill, NJ (US)

( * ) Notice: Subject to any disclaimer, the term of this patent is extended or adjusted under 35 U.S.C. 154(b) by 120 days.

(21) Appl. No.: 10/876,904

(22) Filed: Jun. 25, 2004

(65) Prior Publication Data

US 2004/0242688 A1    Dec. 2, 2004

Related U.S. Application Data

(63) Continuation of application No. 10/159,450, filed on May 31, 2002, now Pat. No. 6,809,210.

(60) Provisional application No. 60/297,549, filed on Jun. 12, 2001.

(51) Int. Cl.
*C07B 53/00*    (2006.01)

(52) U.S. Cl. .................................................... 562/606

(58) Field of Classification Search ...................... None
See application file for complete search history.

(56) References Cited

U.S. PATENT DOCUMENTS

| | | | | |
|---|---|---|---|---|
| 3,256,266 A | * | 6/1966 | Burt | 530/230 |
| 4,824,611 A | * | 4/1989 | Cells | 554/71 |
| 6,087,458 A | * | 7/2000 | Nonaka et al. | 526/89 |

FOREIGN PATENT DOCUMENTS

| | | | |
|---|---|---|---|
| DE | 1133060 | * | 7/1962 |
| GB | 872310 | * | 6/1958 |
| NL | 6411251 | * | 3/1965 |

* cited by examiner

*Primary Examiner*—Karl Puttlitz

(57) ABSTRACT

A method of solvating metal ions in an aromatic organic liquid. The method includes adding an ammonium salt having an organic acid reagent to the aromatic organic liquid. The organic acid reagent comprises a carboxylate having eight (8) or less carbon atoms. Thereafter, an aqueous solution comprising a metal salt is added to the aromatic organic liquid comprising the ammonium salt and the organic acid reagent. As a result, at least 10% by weight of metal ions is solvated in the aromatic organic liquid.

14 Claims, 2 Drawing Sheets

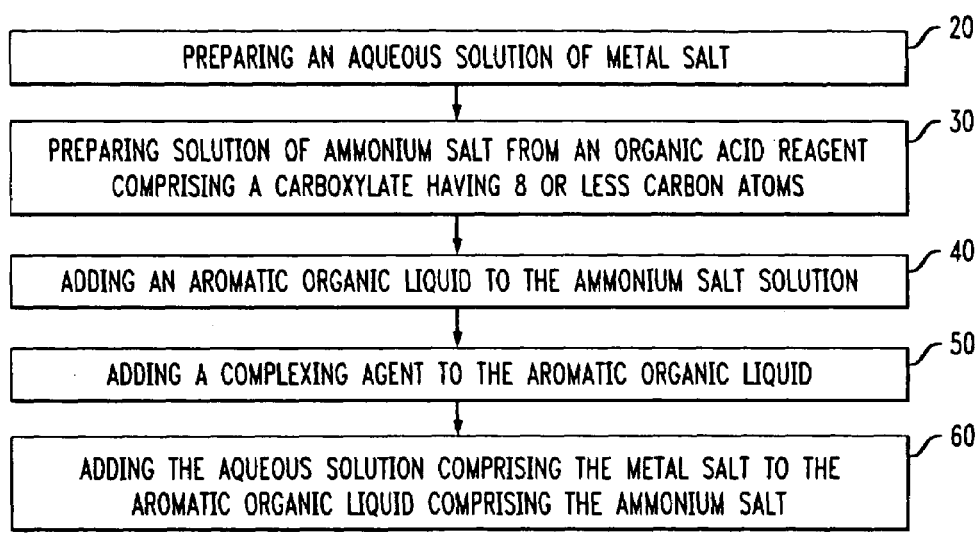
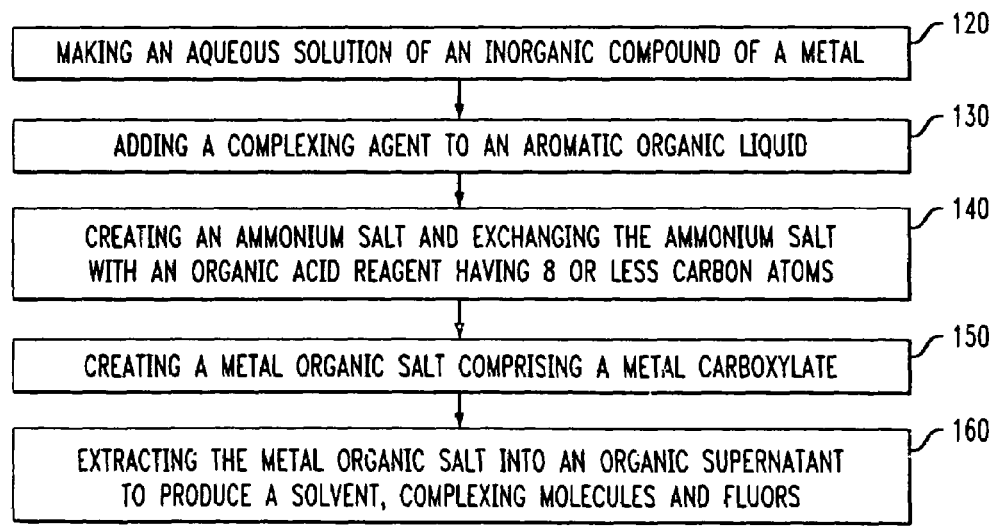

FIG. 3
CARBOXYLIC ACIDS FOR LENS YLS

| | | | |
|---|---|---|---|
| 2C — ACETIC (AcA)[60] | 3C — PROPIONIC (PA)[74] | 4C S — ISOBUTYRIC (IBA)[88] | 4C S — BUTYRIC (BA)[88] |
| 5C — ISOVALERIC (IVA)[102] | 5C — TRIMETHYLACETIC (TMAA)[102] | 5C S — METHYLBUTYRIC (MBA)[102] | 5C S — VALERIC (VA)[102] |
| 6C — 2METHYLVALERIC (MVA)[116] | 6C — ETHYLBUTYRIC (EBA)[116] | 6C — 2,2DIMETHYLVALERIC (DMVA)[130] | 6C S — HEXANOIC (HxA)[116] |
| 8C — ETHYLHEXANOIC (EHA)[144] | | | 9C — TRIMETHYLHEXANOIC (TMHA)[158] |

⟵ WATER SOLUBLE  —  WATER INSOLUBLE ⟶

COMPOSITIONS COMPRISING A SOLVATED METAL

CROSS-REFERENCE TO RELATED APPLICATION

This application claims priority of Provisional Application Ser. No. 60/297,549 which was filed Jun. 12, 2001.

BACKGROUND OF THE INVENTION

I. Field of the Invention

The present invention relates to a method of solvating metal ions in an aromatic organic liquid.

II. Description of the Related Art

It is well known that the solubility of metal ions in an aromatic organic liquid is limited. Aromatic organic liquids are typically hostile for dissolving metal salts. Various techniques have been employed for solvating an inorganic metal salt in an aromatic organic liquid. These methods, however, have proven inadequate for certain applications, particularly those where the optical characteristics of the solvated metal ions are of importance. To date, these known techniques have solvated substantially less than ten percent (10%)—e.g., about one percent (1%)—of the metal ions by weight in the aromatic organic liquid. Using these methods, the solvated metal ions to date have been turbid—e.g., the particles are not homogenously solvated, but are suspended.

The formation of metal salts using transitional metals soluble in an organic hydrocarbon media is known. To date, these solutions have been used in paints, for example, to accelerate drying. The known solutions are typically heterogeneous, as well as optically opaque, thereby scattering light when employed in certain applications. Consequently, homogeneity and/or optical transparency have not become established requirements for these known solutions.

SUMMARY OF THE INVENTION

The present invention provides a method for solvating metal ions in an aromatic organic liquid. More particularly, the method promotes solvating one or more metals, such as Ce, Pr, Nd, Pm, Sm, Eu, Tb, Dy, Ho, Er, Tm, Lu, In, Gd, Pb and Yb, for example, in an aromatic organic liquid. By this method, at least ten percent (10%) by weight of metal ions is solvated in the aromatic organic liquid. Using the method of the present invention, the solvated metal ions may be characterized as homogenous. Moreover, depending on the metal selected, the solvated metal ions may also be optically transparent (e.g., does not substantially scatter light), as well as supporting a solution capable of fluorescence at one or more wavelengths, for example, in response to receiving radiation.

In accordance with the present invention, a reagent is employed for increasing the concentration of a metal ion(s) solvated in an aromatic organic liquid. The reagent may comprise a carboxylate having less than or equal to 8 carbon atoms. An aliphatic carboxylate may be employed, for example, as the reagent.

In an embodiment, an aqueous solution comprising a metal salt is added to an organic liquid comprising an ammonium salt formed from an organic acid reagent. The organic acid reagent increases the amount of metal ions solvated. The stoichiometry of the constituents of the aqueous solution and organic liquid is selected such that this step produces a metal organic salt.

In another embodiment of the present invention, a complexing agent may be used in solvating metal ions. The complexing agent increases the stability of an organic phase created as a result of solvating the metal ions. Here, the complexing agent is added to the organic liquid prior to introducing the aqueous solution comprising the metal salt. Various metal complexing agents may be employed in this regard, such as tri-alkyl phosphine oxide and/or tri-butyl phosphine oxide, for example.

BRIEF DESCRIPTION OF THE DRAWINGS

The present invention will be better understood from reading the following description of non-limiting embodiments, with reference to the attached drawings, wherein below:

FIG. 1 depicts a flow chart of an embodiment of the present invention;

FIG. 2 depicts a flow chart of another embodiment of the present invention; and FIG. 3 depicts another embodiment of the present invention.

It should be emphasized that the drawings of the instant application are not to scale but are merely schematic representations, and thus are not intended to portray the specific dimensions of the invention, which may be determined by skilled artisans through examination of the disclosure herein.

DETAILED DESCRIPTION

The present invention provides for a method of solvating metal ions in an aromatic organic liquid. The resultant solution of present method solvates at least ten percent (10%) by weight of the metal ions in the aromatic organic liquid. By employing the present method, the solvated metal ions may be characterized as homogenous. Moreover, depending on the metal selected, the solvated metal ions may also be optically transparent (e.g., does not substantially scatter light), as well as supporting a solution capable of fluorescence, usually with the addition of a scintillator dye, at one or more wavelengths, for example, in response to receiving radiation. The solvated metal salt solution has various applications, including use in a liquid scintillator, for example.

Referring to FIG. 1, a flow chart 10 of an embodiment of the present invention is illustrated. Flow chart 10 depicts a number of steps performed in executing a method of solvating metal ions in an aromatic organic liquid. The method includes the step of preparing an aqueous solution (20). The aqueous solution is formed from a metal salt. Consequently, the aqueous solution comprises metal ions, for example. The metal salt selected should correspond with the desired metal to be solvated. Thusly, the metal salt may comprise at least one of Ce, Pr, Nd, Pm, Sm, Eu, Tb, Dy, Ho, Er, Tm, Lu, In, Gd, Pb and Yb, for example. Metal salts formed from Ce, Pr, Nd, Pm, Sm, Eu, Tb, Dy, Ho, Er, Tm and/or Lu may be characterized as being colored, lacking optical clarity, and thusly, potentially absorbing light. In contrast, the metal salts formed from In, Gd, Pb and/or Yb, may be optically transparent for use in a liquid scintillator, for example.

The method also includes the step of preparing a solution of ammonium salt (30). The ammonium salt is formed from an organic acid reagent. The organic acid reagent is employed to increase the amount of metal ions solvated. To solvate at least ten percent (10%) by weight of the metal ions, an organic acid reagent is selected having less than or equal to eight (8) carbon atoms. In one embodiment, the organic acid reagent comprises an aliphatic carboxylate having five (5) carbon atoms. It will be apparent to skilled artisans from that instant disclosure detailed herein that the order or sequence in which step (20) and step (30) are performed is not essential to the present invention.

Once the solution of step (30) is prepared, an aromatic organic liquid is added (40) to the solution of ammonium salt. Here, the aromatic organic liquid functions as a solvent for the metal salt of step (20). The aromatic organic liquid may comprise at least one of pseudocumene, 1,2,4 trimethylbenzene, and 1-methylnaphthalene, for example. The purity of these organic liquids may be relevant for certain applications. For example, if the organic liquid is to be used in a liquid scintillator, the resultant solution of the present embodiment should be optically transparent such that light is not absorbed in the region of interest and does not scatter.

In one alternative embodiment of the present embodiment, a complexing agent is added to the aromatic organic liquid (50). The complexing agent, here, is employed to facilitate increased stability of the organic phase of the resultant solvated metal ions. The usage of a complexing agent may be particularly of benefit where the metal ions are solvated in the aromatic organic liquid for large scale, liquid scintillator applications, for example. Here, the complexing agent may comprise at least one of tri-alkyl phosphine oxide and tri-butyl phosphine oxide, for example.

Thereafter, the aqueous solution comprising the metal salt of step (20) and the aromatic organic liquid solution comprising the ammonium salt (40) are added together (60). During this adding step (60), both constituents are added together by any number of known techniques. In one example, the constituents are mixed by a stirring step.

As a result of the hereinabove steps, a two-phase solution is created from an aqueous solution of a metal salt, typically $MX_3$, for example, and an excess if ammonium carboxylate in a conventional metathesis reaction. In the ionized water phase, $NH_4^+X^-$ is formed. Moreover, in the organic phase, a metal organic salt, such as $M(carboxylate)_3$, is formed. Once the adding step (60) is completed, the organic phase may be separated from the byproducts in the water phase. Consequently, the solvent and metal carboxylate are separated such that the solution of the metal organic salt may be washed in water and dried using conventional processes.

In an alternative embodiment, a carboxylic acid may also be added to the aromatic organic liquid solution. This carboxylic acid may be employed to reverse aggregation that may arise in the aromatic organic liquid solution. While substitutes may be apparent to skilled artisan upon reviewing the instant disclosure, the second carboxylic acid may be realized by trimethyl acetic acid ("TMAA").

Referring to FIG. 2, a flow chart 100 of another embodiment of the present invention is illustrated. Flow chart 100 depicts a number of steps performed in executing a method of solvating metal ions in an aromatic organic liquid. The method initially comprises the step of making and reacting an aqueous solution of an inorganic compound of a metal (120). The metal selected may comprise at least one of Ce, Pr, Nd, Pm, Sm, Eu, Th, Dy, Ho, Er, Tm, Lu, In, Gd, Pb and Yb, for example.

In one alternative embodiment of the present invention, a complexing agent is added to an aromatic organic liquid (130). The complexing agent, here, is employed to facilitate increased stability of the organic phase of the resultant solvated metal ions. The usage of a complexing agent may be particularly of benefit where the metal ions are solvated in the aromatic organic liquid for large scale, liquid scintillator applications, for example. Here, the complexing agent may comprise at least one of tri-alkyl phosphine oxide and tri-butyl phosphine oxide, for example.

Thereafter, an ammonium salt is created (140). This step (140) enables the exchange of the created ammonium salt with the organic acid to thereby form a metal organic salt. The organic acid has less than or equal to eight (8) carbon atoms. Consequently, the carboxylate having less than or equal to eight (8) carbon atoms acts as a reagent to increase the amount of metal ion(s) solvated to at least ten percent (10%) by weight. In one embodiment, the organic acid reagent comprises a carboxylate having five (5) carbon atoms.

Subsequently, a metal organic salt is created (150). The metal organic salt of this step (150) is the product of combining the neutralized aqueous solution comprising the metal salt with the liquid solution comprising the ammonium salt in the organic acid reagent in the presence of the aromatic organic liquid. If the organic acid is a carboxylate, the metal organic salt comprises a metal carboxylate.

Thereafter, the metal organic salt is extracted into the organic supernatant on an aqueous solution (160). Upon combining the neutralized aqueous solution with the aromatic organic liquid solution (150), a water phase, as well as an organic phase consisting of the solvent and complexing molecules, if employed. Moreover, the organic phase comprises the metal organic salt, such as, for example a metal carboxylate. This results in metal carboxylate being separated from the underlying aqueous solution.

The selection of the metal salt, the organic acid reagent and the complexing agent in the hereinabove methods are of significance in enabling the step of extraction (160) without interference. Water is pervasively present throughout the steps of the hereinabove methods. However, in accordance with the present methods, water should not create instability or interfere with the extraction step (160).

In an alternative embodiment, a carboxylic acid may also be added to the aromatic organic liquid solution. This carboxylic acid may be employed to reverse aggregation that may arise in the aromatic organic liquid solution. While substitutes may be apparent to skilled artisan upon reviewing the instant disclosure, the second carboxylic acid may be realized by trimethyl acetic acid ("TMAA").

EXPERIMENTAL RESULTS

Referring to FIG. 3, a chart 200 of potentially applicable organic acid reagents is illustrated. Here, several organic acid reagents are illustrated having varying water solubility. A number of experiments were performed with the compounds depicted in chart 200. Using empirical testing, chart 200 may be employed to assist in selecting the appropriate compound(s) for the hereinabove methods. Firstly, the metal carboxylate selected should be water insoluble. This property makes the extraction process much less subject to precise pH matching in the hereinabove methods. Consequently, this may eliminate carboxylates having less than five (5) carbon atoms.

Secondly, the carboxylate selected should have a particular molecular form(s). This criterion depends on the steric hindrance offered by the molecular structure to the complexing agent also employed in the hereinabove methods. The presence of sterically demanding methyl groups, such as, trimethyl hexanoates, for example, may be preferred for certain applications over ethylhexanoates, for example. Ethylhexanoates may result in the formation of a viscous material that scatters light, in contrast with the several methyl groups, which should not result in the aggregation causing light to scatter. It should be noted that the lightest salt by molecular weight of those depicted in chart 200 may be advantageous as well for certain applications.

After the empirical testing, the isovalerate ("IV") was found advantageous under the above criteria. Thereafter, trimethyl acetate was found advantageous under the above criteria. For a liquid scintillator applications, $YbIV_3$ or $InIV_3$, were observed as advantageous as the metal salts of the selected organic acid reagent.

It has been observed by the above reference experimentation that the metal isovalerates dissolve freely in the solvents and are sufficiently clear colorless liquids for various uses, including liquid scintillator applications. Nonetheless, it has been observed within some defined period of time (e.g., between a day or a week), that a solution of metal isovalerates forms a gel, regardless of the loading. Consequently, a complexing agent, such as trialkyl phosphine oxide and/or tributyl phosphine oxide, for example, may be needed to inhibit the $MIV_3$ molecule from polymerization in large-scale applications. Rare earth salts, in particular, tend to form aggregates.

It has been observed that aggregation in the aromatic organic liquid solution in the hereinabove methods may be reversed by adding a small amount of a second carboxylic acid. Initially, isovaleric acid—the organic salt being an isovalerate—was tried in one experiment, but found to cause too much viscosity because of the low steric hindrance of the molecular form. Consequently, it was observed that trimethyl acetic acid ("TMAA") might be advantageous.

From this experiment, the amount of isovaleric acid added may be relevant for certain applications, such as a liquid scintillator, because residual free protons from the acid quench the scintillation light. It has been observed that the quenching was not very severe (e.g., about a 25% loss). To overcome this problem, a second, neutral complexing agent may be added to reduce the otherwise required acid fraction, and thereby also reduce the quenching. Various neutral complexing agents may be employed in this regard, though a number of organophosphorous compounds were found to be advantageous. In order to minimize the amount of organophosphorous material required, compounds offering greater complexing functionality were observed to be more attractive than those offering lesser complexing functionality. In this regard, tri-butyl phosphine oxide ("TPBO") was found advantageous. From the experiments performed, it was found that a final formulation for both Yb and In was $MIV_3$ [TBPOx; TMAAy], where the complexing agent in the square brackets have x and y molar equivalents. The complexing agent was observed to effectively inhibit gelation in the organic solution without introducing deleterious effects.

In one experiment, the following procedure was performed for preparing 0.1 to 1 liter size samples. This procedure was repeated about 50 times at least with a combination of solvents, such as pseudocumene, 1,2,4 tri-methylbenzene, or 1-methylnaphthalene, for example, and initial inorganic compound of a metal, such as a chloride or nitrate, for example. Before mixing the solvent, the proportions used in the procedure were equivalents to about one (1) mole of Yb in the carboxylate sample. The following corresponds with the experimental procedure employed:

1) Preparing one mole of MCl3 or $M(NO_3)_3$ solution in distilled $H_2O$;
2) Neutralizing 4.5 equivalents of IVA (excess by 1.5 equiv.) by 4.5 moles of concentrated ammonium hydroxide, adding excess water after neutralization has been completed;
3) Adding organic phase (x equivalents of TBPO, y of TMAA, pseudocumene or 1 methylnaphthalene for the heaviest loading, typically between 10% to 15%, to support fluorescence in liquid scintillator applications, where convention fluorescent dyes are employed);
4) Adding salt solution of step (1) to step (3) while stirring, to allow the isovalerate to form and immediately dissolve into the organic phase;
5) Gravimetrically separating the organic phase from the water phase; and
6) Drying the organic $MIV_3$[TBPO:TMAA] phrase by filtering through $Na_2SO_4$.

From the hereinabove steps, the components employed in the present method include a solvent into which the metal ions may be solvated or loaded. This may be a known solvent having desirable properties associated with a particular application of the present invention. For example, the solvent may have relatively high light conversion properties, and/or inexpensive. Common solvents include, for example, pseudocumene, 1,2,4 tri-methyl benzene or 1 methylnaphthalene.

Another component employed includes an organic salt of the metal to be loaded. The molecular weight of the salt should be as small as possible. In selecting the smallest molecular weight for the salt, the "baggage" of the metal carrying salt in the solvent should be reduced.

Furthermore, a complexing agent may also be used in the present method. The complexing agent may be an additive for certain large scale, liquid scintillator applications. In certain proportions that "complex" the metal, i.e. surround the metal organic salt in such a way that it: (i) inhibits aggregation/polymerization with other metal organic molecules promoting viscosity, haze, gelling etc; (ii) minimizes trapping of the initial energy from reaching the LS solvent and creating light; and (iii) promotes chemical stability (e.g., precipitation of the salt, as well as other instabilities that can result in (i) and (ii)). The complexing agent may comprise tri-alkyl phosphine oxide or tri-butyl phosphine oxide, for example.

The present method may also employ fluors for liquid scintillator applications. Here, scintillating fluors comprise fluorescent additives for interacting with the solvent. In so doing, light is created at a desired wavelength convenient for photo-multiplier detection.

While the particular invention has been described with reference to illustrative embodiments, this description is not meant to be construed in a limiting sense. It is understood that although the present invention has been described, various modifications of the illustrative embodiments, as well as additional embodiments of the invention, will be apparent to one of ordinary skill in the art upon reference to this description without departing from the spirit of the invention, as recited in the claims appended hereto. It is therefore contemplated that the appended claims will cover any such modifications or embodiments as fall within the true scope of the invention.

The invention claimed is:

1. A composition comprising: a solution including a metal organic salt and an aromatic organic liquid, said metal organic salt including a carboxylate group having eight or less carbon atoms, said metal constituting at least 10% by weight of said solution, in which said metal includes an element selected from the group consisting of Ce, Pr, Nd, Pm, Sm, Eu, Th, Dy, Ho, Er, Tm, Lu, In, Gd, Pb, and Yb.

2. The composition of claim 1 in which said aromatic organic liquid includes a carboxylic acid.

3. The composition of claim 1 in which said metal organic salt is substantially insoluble in water.

4. The composition of claim 1 in which said carboxylate group includes five or more carbon atoms.

5. The composition of claim 1 in which said carboxylate group corresponds to a carboxylic acid selected from the group consisting of: acetic, propionic, isobutyric, butyric, isovaleric, trimethylacetic, methylbutyric, valeric, 2-methylvaleric, ethylbutyric, 2,2-dimethylvaleric, hexanoic, and ethylhexanoic.

6. The composition of claim 1 in which said metal includes an element selected from the group consisting of Ce, Pr, Nd, Pm, Sm, Eu, Th, Dy, Ho, Er, Tm and Lu.

7. The composition of claim 1 in which said metal includes an element selected from the group consisting of In, Gd, Pb, and Yb, and said composition is substantially free from scattering of light in a visible range of wavelengths.

8. The composition of claim 2 in which said carboxylic acid includes trimethyl acetic acid.

9. The composition of claim 5 in which said carboxylate group includes a member selected from the group consisting of isovalerate and trimethylacetate.

10. The composition of claim 9 in which said carboxylate group includes isovalerate.

11. The composition of claim 7 further including a fluorescent scintillator dye, said composition being capable of fluorescence.

12. A composition comprising: a solution including a metal organic salt and an aromatic organic liquid, said metal organic salt including a carboxylate group having eight or less carbon atoms, said metal constituting at least 10% by weight of said solution, where said composition includes an organophosphorus complexing agent, in which said complexing agent includes a trialkyl phosphine oxide.

13. The composition of claim 1 in which said composition includes a complexing agent.

14. The composition of claim 13 in which said complexing agent includes an organophosphorus compound.

* * * * *